(12) United States Patent
Loebl et al.

(10) Patent No.: US 7,498,720 B2
(45) Date of Patent: Mar. 3, 2009

(54) BULK ACOUSTIC WAVE SENSOR

(75) Inventors: Hans Peter Loebl, Monschau-Imgenbroich (DE); Matthias Wendt, Wuerselen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/574,446

(22) PCT Filed: Sep. 28, 2004

(86) PCT No.: PCT/IB2004/051896

§ 371 (c)(1),
(2), (4) Date: Apr. 4, 2006

(87) PCT Pub. No.: WO2005/036150

PCT Pub. Date: Apr. 21, 2005

(65) Prior Publication Data

US 2007/0007851 A1    Jan. 11, 2007

(30) Foreign Application Priority Data

Oct. 8, 2003 (EP) .................... 03103731

(51) Int. Cl.
*H01L 41/04* (2006.01)
*H01L 41/08* (2006.01)

(52) U.S. Cl. .............. 310/335; 310/313 B; 310/313 R; 73/24.01

(58) Field of Classification Search ........... 310/313, 310/335; 73/24
See application file for complete search history.

(56) References Cited

U.S. PATENT DOCUMENTS

| 4,596,697 | A | | 6/1986 | Ballato | |
|---|---|---|---|---|---|
| 5,117,146 | A | * | 5/1992 | Martin et al. | 310/313 R |
| 5,151,110 | A | * | 9/1992 | Bein et al. | 95/140 |
| 5,221,871 | A | * | 6/1993 | Fuchs et al. | 310/313 R |
| 5,325,704 | A | | 7/1994 | Mariani et al. | |
| 5,744,902 | A | | 4/1998 | Vig | |
| 5,936,150 | A | | 8/1999 | Kobrin et al. | |
| 6,025,725 | A | * | 2/2000 | Gershenfeld et al. | 324/652 |
| 6,029,500 | A | * | 2/2000 | Tom | 73/24.06 |
| 6,196,059 | B1 | | 3/2001 | Kosslinger et al. | |
| 6,293,136 | B1 | * | 9/2001 | Kim | 310/313 B |
| 6,626,026 | B2 | * | 9/2003 | Banda et al. | 73/24.01 |
| 6,928,877 | B2 | * | 8/2005 | Carlson et al. | 73/579 |
| 2003/0041654 | A1 | * | 3/2003 | Larson et al. | 73/64.53 |
| 2003/0137216 | A1 | * | 7/2003 | Tamayo de Miguel et al. | 310/311 |
| 2003/0215865 | A1 | * | 11/2003 | Mayer et al. | 435/6 |
| 2006/0125489 | A1 | * | 6/2006 | Feucht et al. | 324/633 |

FOREIGN PATENT DOCUMENTS

WO    WO0143870 A2    6/2001

* cited by examiner

*Primary Examiner*—Jaydi SanMartin

(57) ABSTRACT

A sensor includes a substrate 1 and at least one resonator, which includes an acoustic reflector 2, a piezoelectric layer 5, a first and second electrode 3, 4 placed on the same side of the piezoelectric layer 5, and a sensing layer 6. The sensing layer 6 reacts with a chemical or biological agent by absorption, adsorption, desorption or chemical reaction. As a result the individual frequency of a resonator changes and conclusions about the agent can be drawn. Such a sensor is very sensitive to an agent being sensed, especially when used in liquids.

6 Claims, 1 Drawing Sheet

BULK ACOUSTIC WAVE SENSOR

This invention relates to a sensor comprising a substrate and at least one resonator, said resonator is comprised of an acoustic reflector, a piezoelectric layer, a first and a second electrode, and a sensing layer.

The rapid and accurate detection of chemical and biological agents is very important for many activities such as environmental pollution testing or military application.

Heretofore, biological/chemical sensors have been based on either calorimetric or gravimetric effects.

For example, U.S. Pat. No. 5,936,150 describes a chemical sensor using a thin film acoustic resonator coated with a chemically sensitive sorbent coating. The thin film acoustic resonator has electrodes separated by a thin film piezoelectric layer and is supported by a multilayer resonant acoustic isolator. In order to detect a chemical, the chemical of interest (usually a vapor) is brought into contact with and interacts with the exposed sorbent surface coating, causing the mass and/or the mechanical properties of the sorbent coating to change. The changes in the sorbent coating will cause a change in the resonant frequency of the thin film acoustic resonator, as the coating lies directly upon the resonator and is part of the acoustic resonant path.

The above-mentioned sensor may best be applied when detecting gaseous agents. When using the sensor in liquids the liquid will attenuate the resonator. This results in a lower sensitivity and a lower Q factor of the device.

It is an object of the present invention to provide a sensor that is more sensitive when used in liquids.

This is achieved by a sensor comprising a substrate and at least one resonator, said resonator is comprised of an acoustic reflector, a first and a second electrode, a piezoelectric layer, and a sensing layer wherein the first and the second electrode are placed on the same side of the piezoelectric layer.

Such a resonator has the advantage that predominately shear vibrations are excited that may not be absorbed by liquids. As a result the excited vibrations cannot propagate in the liquid and the attenuation of the vibrations is low. This results in lower acoustic losses of the resonator. A sensor made of such a resonator has a high sensitivity when used in liquids.

The sensor includes a resonator having a low electric impedance.

In accordance with the invention, a highly robust and sensitive sensor array for the detection of chemical or biological agents in liquids is obtained.

A sensor in accordance with the invention works with a very high sensitivity since every material used in the sensing layers interacts in a different degree with the agent to be detected. The obtained output signal is rather complicated and thus sensitive to the agent to be detected.

Figure 1:
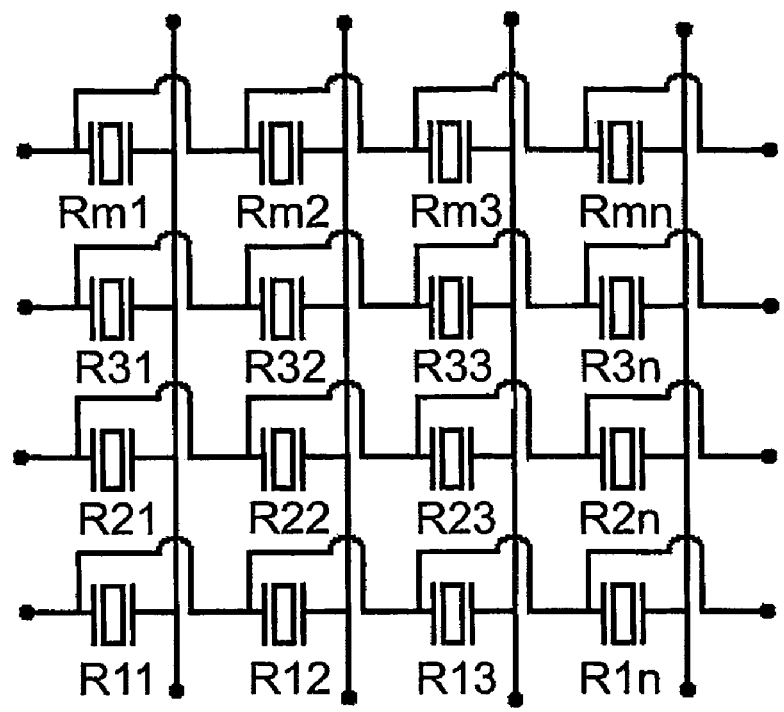
Figure 2:
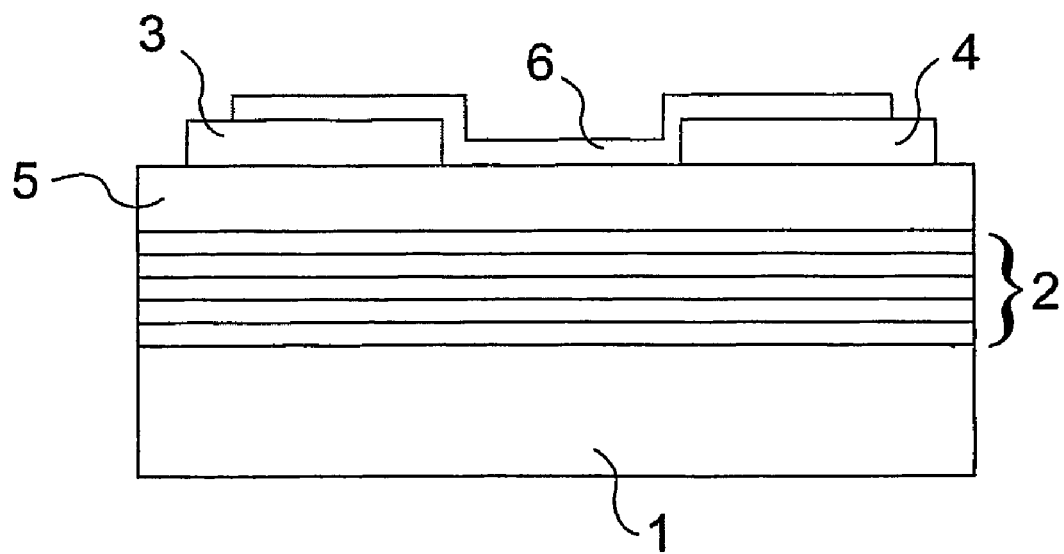

The invention will be explained in more detail below with reference to two drawings. In the drawings FIG. 1 shows a sensor array circuitry and FIG. 2 shows the construction of a resonator in cross-section.

The sensor according to the invention comprises a substrate and at least one resonator. Said resonator is comprised of an acoustic reflector, a first and a second electrode, a piezoelectric layer, and a sensing layer.

More preferred the sensor comprises a plurality of individually addressable resonators. It is highly preferred that this plurality of resonators is arranged in a rectangular row and column configuration including m rows and n columns. By this arrangement a sensor array is achieved. Most preferred each resonator might be addressed individually. FIG. 1 shows a circuitry of such a sensor array comprising m·n resonators R.

If the sensor comprises a plurality of resonators, each of the resonators is separated from its neighboring resonators by such a distance that the resonant energies do not overlap.

The sensor comprises a substrate 1 which may comprise a semiconducting material such as Si or GaAs or an insulating material such as glass or $Al_2O_3$. The resonators are deposited on the substrate 1. Each resonator comprises an acoustic reflector 2, a first electrode 3 and a second electrode 4, a piezoelectric layer 5, and a sensing layer 6.

FIG. 2 shows in cross-section a resonator according to the invention.

Most preferred the acoustic reflector 2 has a layered structure and comprises several layers having alternating high and low acoustic impedance. These layers show a thickness of ¼ of the resonance wavelength λ. The layers having low acoustic impedance may for example comprise an organic or inorganic aerogel, an organic or inorganic xerogel, a foam, a low density synthetic material or $SiO_2$. The layers having a high acoustic impedance may for example comprise $Ta_2O_5$, $Si_3N_4$, $TiO_2$, ZnO, $LiNbO_3$, $LiTaO_3$, $Al_2O_3$, SiC, $V_2O_5$, $Nb_2O_5$, $ZrO_2$, $La_2O_3$, $WO_x$ (0<x≦3), $MoO_x$ (0<x≦3), ZrC, WC, MoC, $ThO_2$, $CeO_2$, $Nd_2O_3$, $Pr_2O_3$, $Sm_2O_3$, $Gd_2O_3$, $ReO_x$ (0<x≦3.5), $RuO_2$, $IrO_2$, $Y_2O_3$, $Sc_2O_3$, $LiGeO_2$, $Bi_{12}GeO_{20}$, $GeO_2$, MgO, yttrium-aluminium-garnet ($Y_3Al_5O_{12}$, YAG), yttrium-iron-garnet ($Y_3Fe_5O_{12}$, YIG), $LiGaO_2$, $HfO_2$, AlN, a high density synthetic material, W or C.

The number of layers in the acoustic reflector 2 is odd-numbered and the first and the last layer of the layered structure comprise a material having low acoustic impedance. It should be understood that although five such layers are shown, a greater number may be used, and in general five to nine layers are desirable.

The piezoelectric layer 5 that is placed on top of the acoustic reflector 2 comprises most preferentially AlN. Alternatively ZnO, $KNbO_3$, lead zirconate titanate (PZT), lanthanum-doped lead zirconate titanate (PLZT) or the like may be used in the piezoelectric layer 4

The first and second electrode 3, 4 are deposited on top of the piezoelectric layer 5. The electrodes 3, 4 may comprise a metal like Pt, Al, Al:Cu, Al:Si, Mo, W or an alloy as well as an additional adhesion layer comprising Ti, Cr, or NiCr. Most preferred the two electrodes 3, 4 are interdigitated electrodes.

At the outer side of the piezoelectric layer 5 ground metallizations and/or bond-pads (not shown) are present. The ground metallization and the bond pads may comprise Al, Al:Si, Al:Cu, Cu, Ni, Au or combinations thereof.

A sensing layer 6 completely or only partly covers the two electrodes 3, 4. The material of the sensing layer 6 is selected with respect to the agent to be detected. The detection of the chemical or biological agents is done by absorption, adsorption, desorption or chemical reaction.

The chemical or biological agents may comprise an atom, ion, molecule, macromolecule, organelle, or a cell. The chemical or biological agents may also comprise a substance in a medium including but not limited to, environmental contaminants such as trichloromethane, tetrachloromethane, trichloroethane, trichloroethylene, tetrachloroethane, tetrachloroethylene, toluene, benzene, aromatic compounds and hydrocarbon pesticides. The term "medium" as used herein means an aqueous medium, a non-aqueous liquid medium, and gases. As used herein, the terms "chemical agent" or "biological agent" also include molecules, such as proteins, glycoproteins, metal salts, ions, and the like. The terms also include neurotransmitters, hormones, growth factors, cytokines, monokines, lymphokines, nutrients, enzymes, and receptors. The terms "chemical agent" or "biological agent" also means structured elements such as macromolecular structures, organelles and cells, including, but not limited to, cells of ectodermal, mesodermal, and endodermal origin such as stem cells, blood cells, neural cells, immune cells, and gastrointestinal cells, and also microorganisms, such as fungi, viruses, bacteria, and protozoa.

The sensing layer 6 may for example comprise chemical reactants, antibodies, fragments of antibodies capable of binding an agent, biological receptors for particular agents, enzymes, proteins, oligonucleotides, nucleic acids (such as DNA or RNA), peptides, metallo-organic materials, or small molecules such as ligands. The sensing layer 6 may also comprise a polymeric material that responds to the agent being present at the sensing layer 6. Additionally, the polymeric material of sensing layer 6 can be modified by incorporating molecular groups that will enhance selectivity toward target agents.

In some instances it may be difficult to obtain substances that are specific to a single chemical or biological agent, but the presence of a plurality of resonators allows one to use several materials in the sensing layers 6, one on each resonator. Each sensing layer 6 might have a different reactivity or sensitivity to the chemical or biological agent being sensed. By putting together the information from the group of resonators, the presence of the suspected agent may be inferred. Using materials on the resonators that operate by absorption, adsorption, desorption or chemical reaction, the individual frequencies may go up or down with exposure.

Alternatively the sensor may only be comprised of two resonators. In this embodiment, one of the resonators is a reference resonator and the sensing layer 6 is inactive to the agent. For example, if the detection of the agent is done by absorption, the reference resonator does not change its mass due to absorption because of an inactive coating. Alternatively, the reference resonator comprises a material in the sensing layer 6 from which a known fixed grade of absorption is known.

A resonator comprising both electrodes 3, 4 on the same side of the piezoelectric layer 4 has the advantage that predominately shear vibrations are excited that may not be absorbed by liquids. As a result the excited vibrations cannot propagate in the liquid and the attenuation of the vibrations is low. This results in lower acoustic losses of the resonator. A sensor made of such a resonator or a plurality of such resonators has a higher sensitivity.

The application of a voltage to the electrodes 3, 4 causes the piezoelectric layer 5 to be excited into oscillations. For this reason the first electrode 3 and the second electrode 4 of a resonator are further coupled to an oscillator circuit, capable of applying a time varying excitation voltage between the first electrodes 3 and second electrodes 4, so that a time-varying electric field is generated.

The invention claimed is:

1. A sensor comprising a substrate and a plurality of individually addressable resonators, each of the resonators comprising:
   an acoustic reflector on the substrate, the acoustic reflector comprising a plurality of layers having alternating high and low acoustic impedances, an uppermost layer having the low impedance;
   a piezoelectric layer separated from the substrate by the acoustic reflector;
   first and second resonator electrodes on an upper surface of the piezoelectric layer; and
   a sensing layer covering a portion of an upper surface of each of the first and second resonator electrodes.

2. The sensor of claim 1, wherein the first and the second electrodes are interdigitated electrodes.

3. The sensor of claim 1, wherein the sensing layers the plurality of resonators comprise different materials.

4. The sensor of claim 1, wherein the plurality of layers of the acoustic reflector is an odd number of layers.

5. The sensor of claim 1, wherein the portion of the first and second resonator electrodes covered by the sensing layer comprises a portion of an upper surface of each of the first and second resonator electrodes.

6. A sensor comprising:
   a substrate;
   an acoustic reflector on the substrate, the acoustic reflector comprising a plurality of layers having alternating high and low acoustic impedances, outermost layers of the plurality of layers having the low impedance;
   a piezoelectric layer on the acoustic reflector;
   first and second resonator electrodes on a same surface of the piezoelectric layer; and
   a sensing layer contacting each of the first and second resonator electrodes,
   wherein the sensing layer covers only a portion of each of the first and second resonator electrodes.

* * * * *